(12) United States Patent
Patel

(10) Patent No.: US 10,856,784 B2
(45) Date of Patent: Dec. 8, 2020

(54) SENSOR INITIALIZATION METHODS FOR FASTER BODY SENSOR RESPONSE

(71) Applicant: Medtronic MiniMed, Inc., Northridge, CA (US)

(72) Inventor: Anuj M. Patel, Sherman Oaks, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 602 days.

(21) Appl. No.: 15/639,116

(22) Filed: Jun. 30, 2017

(65) Prior Publication Data
US 2019/0000358 A1 Jan. 3, 2019

(51) Int. Cl.
| | | |
|---|---|---|
| A61B 5/145 | (2006.01) | |
| A61B 5/1486 | (2006.01) | |
| A61B 5/1495 | (2006.01) | |
| A61B 5/00 | (2006.01) | |
| G01N 27/327 | (2006.01) | |

(52) U.S. Cl.
CPC ........ *A61B 5/14532* (2013.01); *A61B 5/1495* (2013.01); *A61B 5/14865* (2013.01); *A61B 5/7203* (2013.01); *A61B 5/14503* (2013.01); *A61B 2562/02* (2013.01); *G01N 27/3277* (2013.01)

(58) Field of Classification Search
CPC ............ A61B 5/14532; A61B 5/14865; A61B 5/1495; A61B 5/7203; A61B 5/14503; A61B 2562/02; G01N 27/3277
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |

(Continued)

OTHER PUBLICATIONS

PCT International Search Report and Written Opinion dated Jan. 3, 2019, International Application No. PCT/US2018/039331.

*Primary Examiner* — Eric F Winakur
*Assistant Examiner* — Abid A Mustansir
(74) *Attorney, Agent, or Firm* — Gates & Cooper LLP

(57) ABSTRACT

A method of initializing a sensor with a voltage sequence including a ramped voltage combined with a biphasic voltage pulse. The initialization scheme results in faster in-vitro sensor run-in and stabilization times. In various examples, the in-vitro sensor stabilization time is reduced from 200 minutes to 40-55 minutes (a reduction by a factor of least 5 as compared to a non-initialized sensor). In addition, staircase voltage initialization is implemented adaptively so that the voltage step size and sweep rates are changed depending on the state of the sensor (characterized by ISIG magnitude). As a result, individual sensors can be initialized in a customized manner rather than by using a general hardwired and harsh initialization scheme.

17 Claims, 20 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0025238 A1 | 2/2010 | Gottlieb et al. |
| 2010/0160861 A1 | 6/2010 | Causey, III et al. |
| 2014/0135605 A1 | 5/2014 | Gottlieb et al. |

SENSOR INITIALIZATION METHODS FOR FASTER BODY SENSOR RESPONSE

TECHNICAL FIELD

The invention relates to a method and apparatus for making and/or initializing an analyte sensor.

BACKGROUND OF THE INVENTION

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g. change in electrical current) through one or more electrodes.

In conventional sensor start-ups, there is a significant delay before the sensor becomes stabilized enough to start sensing, thereby complicating care in clinical settings. In addition, in individuals using analyte sensors in non-hospital settings (e.g. diabetics using glucose sensors to manage their disease), relatively long sensor initialization and/or start-up periods following sensor implantation can be problematical due to both the inconvenience to the user as well as the delayed receipt of information relating to user health. Because many diabetics do not have medical training, they may forgo optimal monitoring and modulation of blood glucose levels due to complexities associated with such management, for example, a two hour start-up period which can be an inconvenience in view of a patient's active daily routine.

For the above-noted reasons, methods and sensor systems that are designed to reduce sensor initialization and/or start-up times are desirable.

SUMMARY OF THE INVENTION

The present disclosure reports on a novel sensor initialization and warm up scheme resulting in faster sensor start up and improved sensor performance. The initialization applies a voltage sequence including a combination of a biphasic voltage pulse and a ramped voltage (e.g., a staircase voltage).

When applied to a typical glucose sensor embodiment generating electrical current (e.g., ISIG) in response to the presence glucose, the initialization scheme:
  lowers the electrical current generation during the initialization (INIT) phase, resulting in reduced metal (e.g., chrome) loss from the sensor; and
  improves day 1 in-vivo performance (characterized by lower time to electrical current stability), a critical advantage for practical implementation and factory calibration.

The data presented herein shows that the sensor signals (ISIG) generated during a staircase voltage initialization scheme are representative of the electrode surface state. Reaching the working over potential in an engineered fashion while initializing the sensor is achievable by applying voltage steps of different magnitude with different sweep rates (e.g., application of a voltage ramp or bi/mono phasic pulse). Thus, voltammetric analysis (e.g., Electrochemical Impedance Spectroscopy (EIS)) may be used to adaptively tailor or customize the initialization process for a particular sensor, e.g., so as to account for variations in physiological and/or manufacturing environments. Illustrative embodiments describe a voltammetric analysis of the sensor that differentiates voltages that drive a non-faradiac/charging current (due to charge redistribution across sensor) from voltages that drive a faradaic current (due to reactions involving various species of redox couples). In one example, the electrical current as a function of the ramped voltage is measured so as to determine the threshold voltage in the ramped voltage at and above which the electrical current is faradaic, so that when the initialization voltage sequence is transmitted to the working electrode, an initial voltage in the initialization voltage sequence is at least equal to, or within 5%, of the threshold voltage, so as to form the metal having a stable (steady state) charge distribution. Thus, as described herein, the voltage reference level best suited to start the initialization process for a particular sensor can be determined from the voltammetric analysis.

In one or more examples, the ramped voltage is stepped from an initial voltage (V_init), that drives current in a charge re-distribution or double layer regime only, through to a final voltage (V_final), the sensor operating potential. Examples of the initial voltage include, but are not limited to, voltages in a range of 250-450 mV. Examples of the final voltage include, but are not limited to, voltages in a range of 400 mV-600 mV. Moreover, the voltage step in the ramped voltage and the voltage sweep rate can be adjusted so that the ramped voltage is ramped in less than 1 hour from the initial voltage to the final voltage and the charge distribution. In one or more examples, the initialization voltage changes a charge distribution of the metal so that, after less than 1 hour from when the initialization voltage is first applied, the electrical current generated in response to the analyte is in 5% agreement with a 2 hour moving average electrical current value and in 10% agreement with a steady state (non-transient) electrical current.

In illustrative embodiments, a voltage generation circuit (e.g., an application specific integrated circuit, ASIC) generates the initialization voltage and a potentiostat transmits the initialization voltage to a working electrode in the sensor. An ASIC generating at least 22 different frequencies can be used to modulate the staircase voltage, thereby enabling a more efficient and optimized voltammetric analysis and initialization protocol. Thus, as described herein, the ramped voltage may be modulated or superimposed with a biphasic pulse having a range of frequencies (e.g., a frequency in a range of 0.1 Hz to 100 kHz).

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

As shown in FIG. 5, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

DETAILED DESCRIPTION OF THE INVENTION

Figure 1:
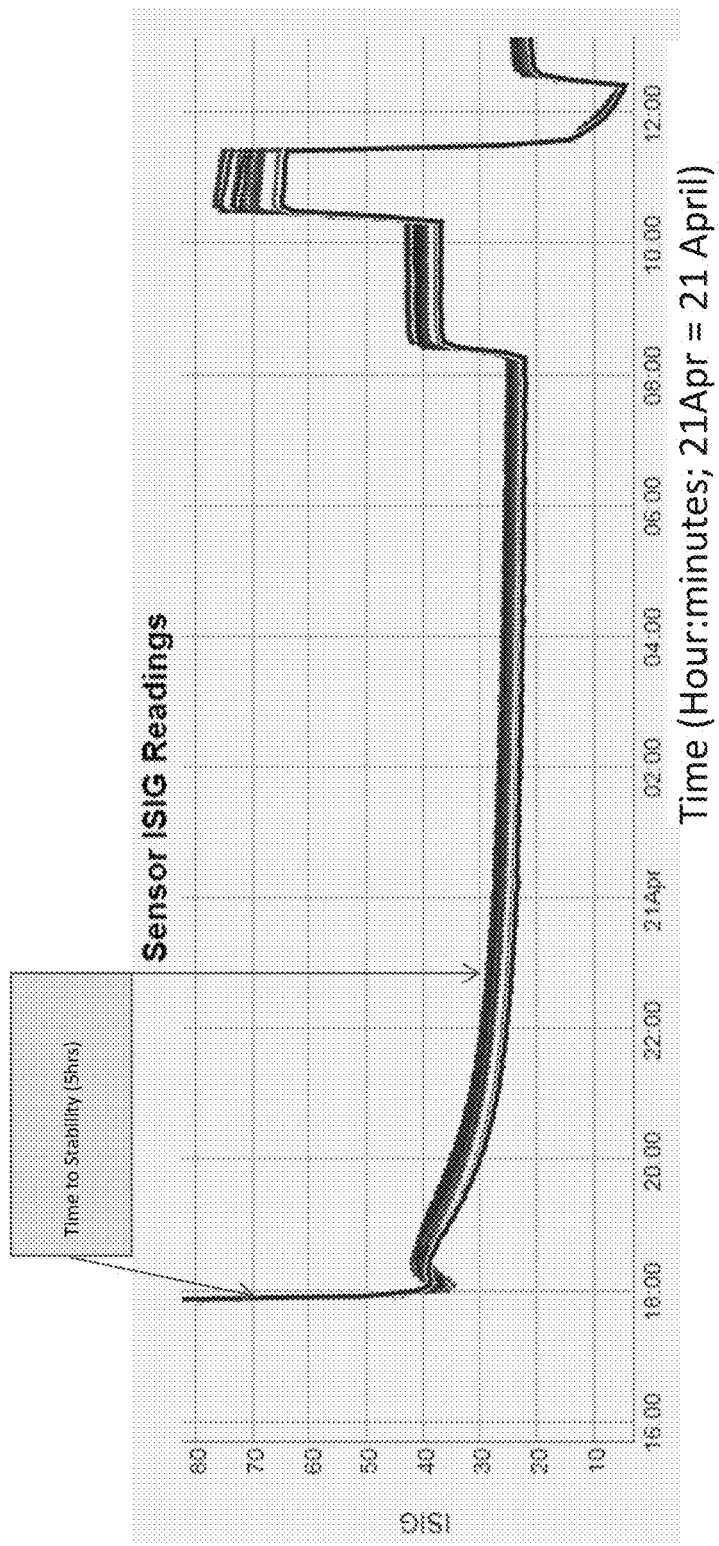
FIG. 1 illustrates ISIG data from a Harmony 1 sensor that was run with no initialization at 400 mV, showing longer run-in time.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a thickness) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

A. Illustrative Embodiments of the Invention and Associated Characteristics

Conventional initialization schemes used with Enlite and Enlite Enhance sensors apply a high voltage pulse that generates high sensor ISIG and leads to chrome loss from the sensors. To counter the chrome loss encountered during harsh sensor initialization and improve in-vitro responses (better oxygen response), Harmony 1 sensors conventionally do not use an initialization scheme. As a result, the Harmony 1 sensors take much longer to achieve stable operation, marring the in-vivo day 1 sensor performance (see FIG. 1).

TABLE 1

Harmony 1 data for a sensor run with no initialization at 400 mV

| DUT | Run-in time (minutes) | Run-in ISIG (nA) | First Stable Point (min) | First Stable ISIG (nA) |
|---|---|---|---|---|
| 1-1 | 200 | 30.12 | 315 | 27.39 |
| 1-2 | 190 | 30.87 | 300 | 28.09 |
| 2-1 | 200 | 29.44 | 315 | 26.77 |
| 2-2 | 225 | 29.38 | 335 | 26.89 |
| 3-1 | 195 | 29.3 | 305 | 26.72 |
| 3-2 | 195 | 29.79 | 305 | 27.16 |
| 4-1 | 190 | 30.3 | 300 | 27.55 |
| 4-2 | 210 | 30.6 | 320 | 27.88 |
| 5-1 | 240 | 29.7 | 350 | 27.13 |
| 5-2 | 230 | 30.26 | 335 | 27.53 |
| 6-1 | 230 | 30.08 | 350 | 27.44 |
| 6-2 | 195 | 31.52 | 300 | 28.82 |
| 7-1 | 185 | 30.78 | 285 | 28.22 |
| 7-2 | 185 | 30.96 | 285 | 28.27 |
| 8-1 | 185 | 27.86 | 295 | 25.36 |
| 8-2 | 195 | 26.79 | 300 | 24.49 |
| Mean | 203.13 | 29.86 | 312.19 | 27.23 |

The data in Table 1 shows that without sensor warm up or initialization:
the time to reach stability (time where ISIG is in 5% agreement with a 2 hr moving average ISIG value) is about 300 minutes (5 hrs); and
the time taken to achieve run-in (ISIG that is in 10% agreement with a stable ISIG) is long—about 200 minutes (3.33 hrs).

Figures 2A, 2B:
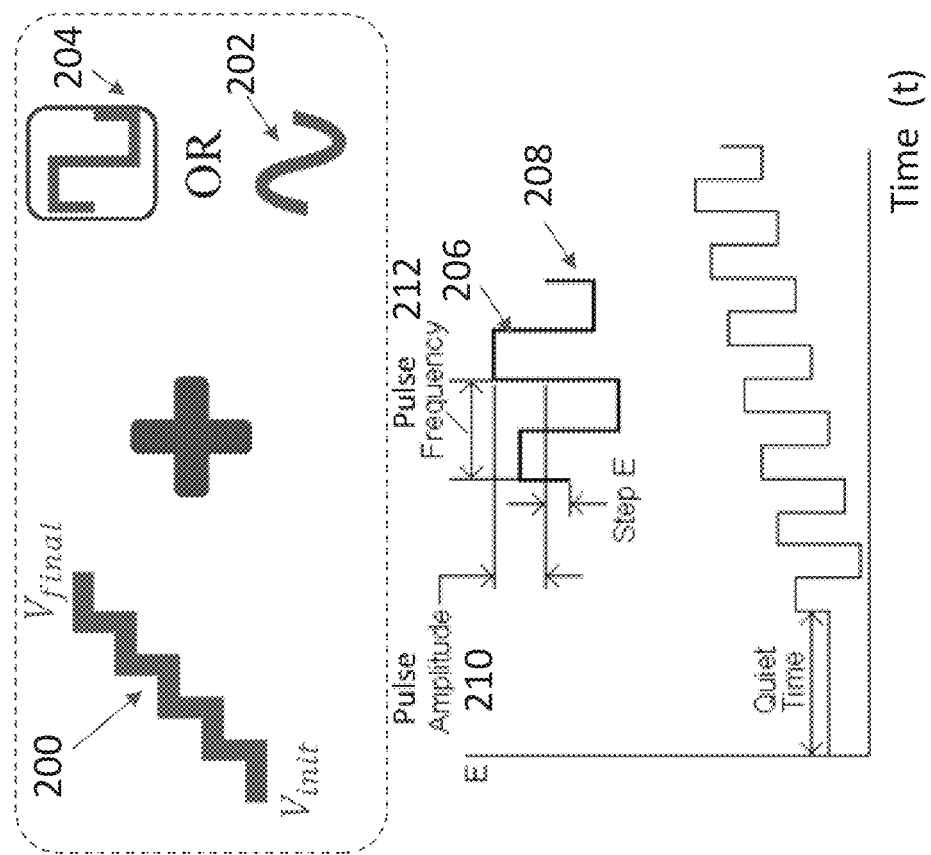
FIG. 2A illustrates superposition of a biphasic sine or square wave with a staircase voltage.
FIG. 2B illustrates a biphasic square pulse of constant amplitude super imposed on a stair case voltage and employed in an initialization scheme, plotting voltage (E) as a function of time (t).

FIGS. 2A and 2B illustrate an initialization scheme comprising modulation of a staircase voltage 200 with a balanced or imbalanced biphasic pulse (e.g., a sine 202 or square 204 voltage pulse), according to embodiments of the invention, wherein the voltage is stepped from $V_{init}$ (driving a current in a charge re-distribution or double layer regime only) to $V_{final}$ (the sensor operating potential).

FIG. 2B illustrates a biphasic pulse 202, 204 is a voltage or charge pulse comprising of alternating anodic 206 and cathodic phases 208 with respect to a reference level (positive and negative pulses with respect to a reference level). A biphasic pulse can begin with either an anodic phase 206 or a cathodic phase 208 and end with a reversed phase/polarity pulse, for example. If the magnitude of net voltage or charge applied to the electrode through a biphasic pulse 202, 204 is zero, the biphasic pulse is a balanced pulse. If the magnitude of net voltage or charge applied to the electrode surface through a biphasic pulse 202, 204 is non zero, the biphasic pulse is an imbalanced pulse. The pulse amplitude 210, pulse frequency 212, and voltage step E are also shown.

As demonstrated herein, the initialization technique comprising adding ("+" in FIG. 2B) the biphasic pulse 202, 204 to staircase voltage 200 initializes the sensor faster than without initialization. Such an initialization scheme comprising biphasic pulses (e.g., of constant amplitude) super imposed on the stair case voltage provide at least two advantages:
significant improvement to day 1 in-vivo performance, as characterized by a reduced sensor run-in time (time to ISIG stability); and
reduced chrome loss and improved longevity of the sensor (a milder sensor warm up ensures that the seed layer surface of the sensor remains intact, improving the longevity of the sensor).

Moreover, as detailed herein, voltammetric analysis of the sensor enables charging and faradic current to be differentiated so as to provide an excellent platform for intelligent and adaptive sensor warm/up. For example, staircase voltammetry analysis of the sensors shows that the generation of ISIG (charging and faradaic currents) depends on the voltage jump and the previous state (charge distribution) of the metal (e.g., platinum) in the working electrode. Based on this analysis, the present disclosure describes algorithms that tailor initialization schemes so as to cater to patient variability (physiological differences) and sensor to sensor variability, e.g., due to variations in the manufacturing of the electrode and other chemically active layers in the sensor. Thus, the present invention provides initialization schemes that transform the physical and/or chemical properties of various layers (electrodes and/or other chemically active layers) in the sensor, so as to achieve a sensor having the surprising and unexpected combination of improved performance and faster start up times.

B. Illustrative Analyte Sensor Constituents Used in Embodiments of the Invention The following disclosure provides examples of typical elements/constituents used in sensor embodiments of the invention. While these elements can be described as discrete units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Figure 3:
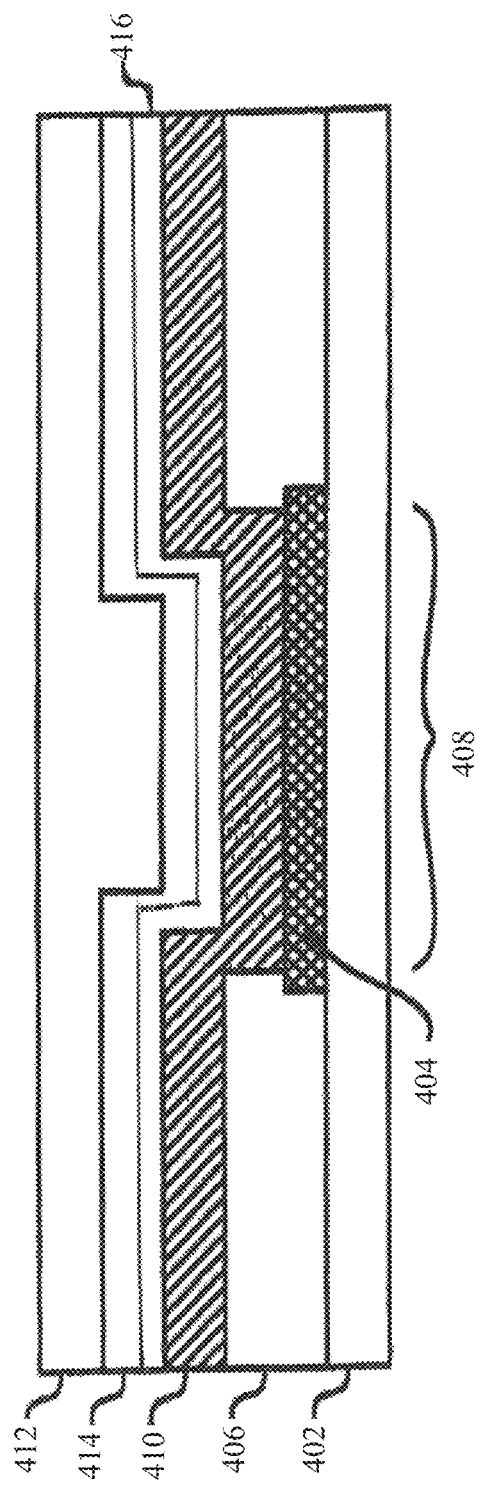
FIG. 3 shows illustrations of amperometric analyte sensors formed from a plurality of planar layered elements.

Sensors of the invention typically include a base constituent (see, e.g. element 402 in FIG. 3). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode comprising a metal for contacting an analyte or its byproduct (e.g. oxygen and/or hydrogen peroxide) to be assayed (see, e.g. element 404 in FIG. 3). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 3.2× working electrode and a 6.3× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant applied potential. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g. element 410 in FIG. 3). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 3). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 3). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltrimethoxysilane.

Analyte Modulating Constituent

The electrochemical sensors of the invention include an analyte modulating constituent disposed on the sensor (see, e.g. element 412 in FIG. 3). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally, such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents, which are typically electrically insulating protective constituents (see, e.g. element 406 in FIG. 3). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Illustrative Sensor Stacks

An embodiment of the invention having a layered stack of constituents is shown in FIG. 3. FIG. 3 illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 3. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 3 includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 3, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by a sputtering process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

Figure 12:
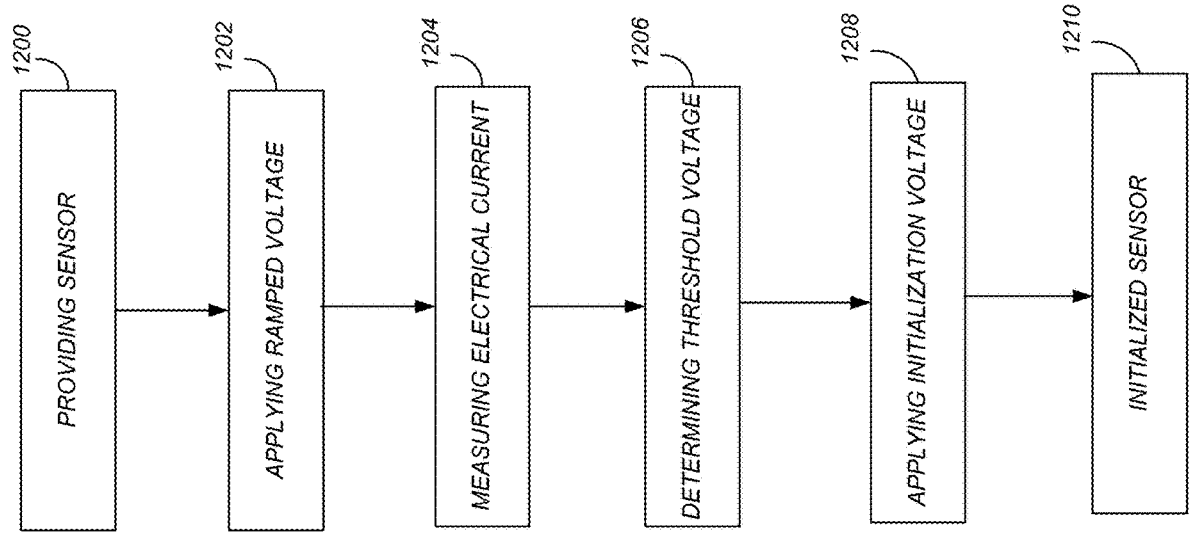
FIG. 12 is a flowchart illustrating a method of making a sensor according to one embodiment.

In certain embodiments of the invention, an adhesion promoter layer 414 is disposed between the analyte modulating layer 412 and the analyte sensing layer 410 as shown in FIG. 12 in order to facilitate their contact and/or adhesion. In a specific embodiment of the invention, an adhesion promoter layer 414 is disposed between the analyte modulating layer 412 and the protein layer 416 as shown in FIG. 3 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising a sputtered platinum electrode composition as disclosed herein, a transmitter and receiver and a glucose meter. In this system, radio signals from the transmitter can be sent to the pump receiver at regular time periods (e.g. every 5 minutes) to provide real-time sensor glucose (SG) values. Values/graphs can be displayed on a monitor of the pump receiver so that a user can self monitor blood glucose and deliver insulin using their own insulin pump. Typically the sensor systems disclosed herein can communicate with other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 4:
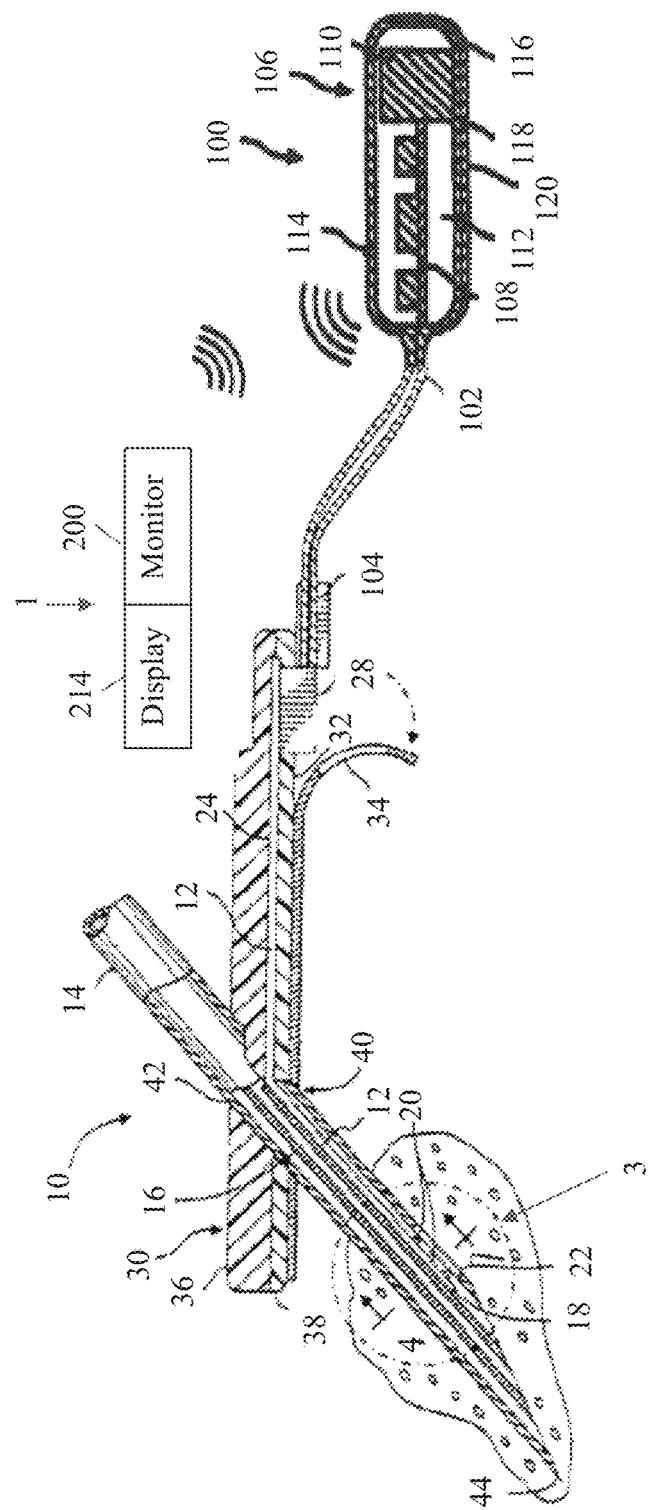
FIG. 4 provides a perspective view illustrating one type of subcutaneous sensor insertion set, a telemetered characteristic monitor transmitter device, and a data receiving device, elements that can be adapted for use with embodiments of the invention.

FIG. 4 provides a perspective view of one generalized embodiment of subcutaneous sensor insertion system that can be adapted for use with the sensor electrodes disclosed herein and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 4 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The base is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 4, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 402 through a connector 104 that is electrically coupled to the connector block 28 of the connector portion 24 of the sensor set 10.

In the embodiment shown in FIG. 4, the telemetered characteristic monitor 400 includes a housing 106 that supports a printed circuit board 108, batteries 110, antenna 112, and the cable 202 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 200 is ready for use.

In the illustrative embodiment shown in FIG. 4, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 4, the sensor electrodes 10 may be used in a variety of sensing applications and may be configured in a variety of positions on a base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 4, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 402 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 5:
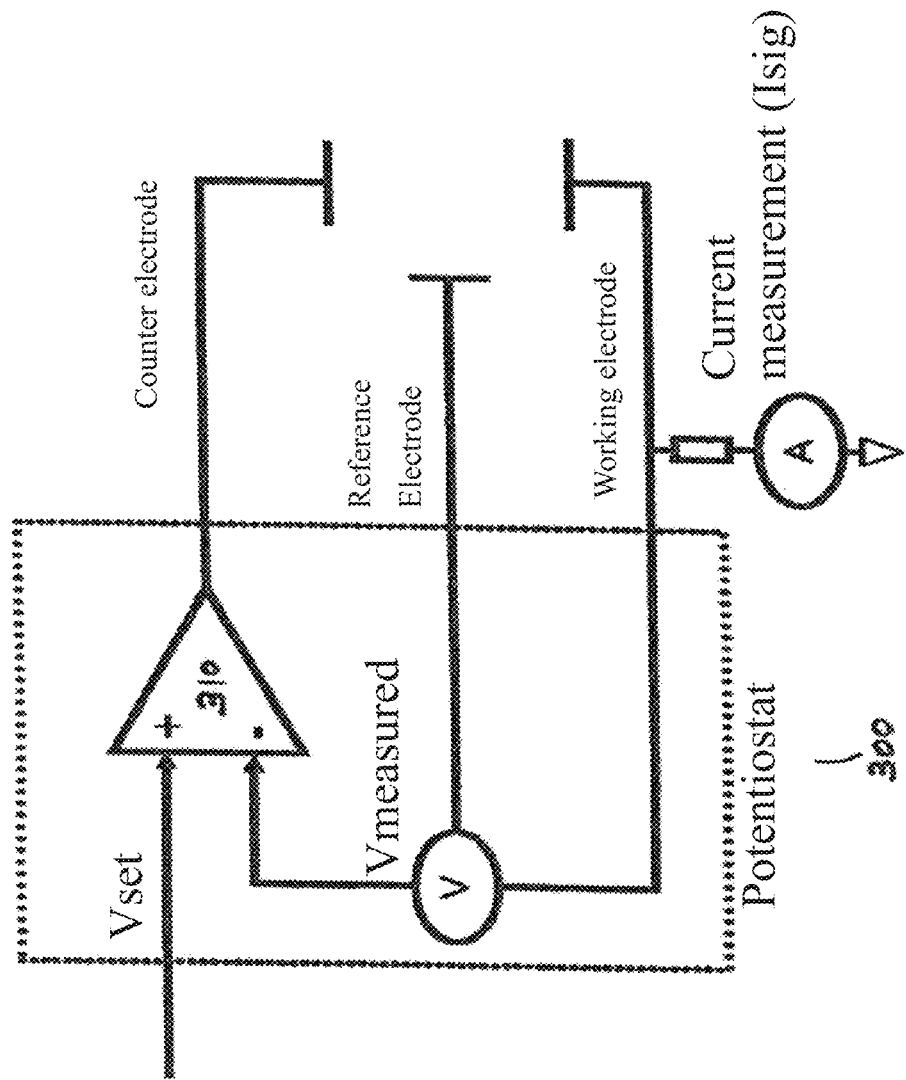
FIG. 5 shows a schematic of a potentiostat that may be used to measure current in embodiments of the present invention.

FIG. 5 shows a schematic of a potentiostat that may be used to measure current in embodiments of the present invention. As shown in FIG. 5, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

EXAMPLES

Common acronyms used in the examples include: WE Working Electrode; GOx Glucose Oxidase; HSA Human Serum Albumin; SITS Sensor In-vitro Test System; GLM Glucose Limiting Membrane (an embodiment of an analyte modulating layer); OQ Operational Qualification; SAR Surface Area Ratio; BTS Bicarbonate Test System; and EIS Electrochemical Impedance Spectroscopy. Dog tests are used to evaluate glucose sensor performance in vivo (Isig and calculated blood glucose level) in diabetic and non-diabetic dogs for up to 3 days and compares glucose level measured by continuous glucose sensors to that measured by a glucose meter.

Experimental Data

The following experiments demonstrate methods for improving control of ISIG behavior during and post initialization.

The stability criteria/specifications used for assessing the sensor performance are:
Run in agreement with respect to a stable point (the time to reach stability): the time where ISIG is in 5% agreement with a 2 hr moving average ISIG value).
Stable signal point percentage agreement (the time taken to achieve run-in): ISIG that is in 10% agreement with a stable ISIG).

1. First Input Voltage Sequence Example (Harmony 1 Sensor)

Figure 6:
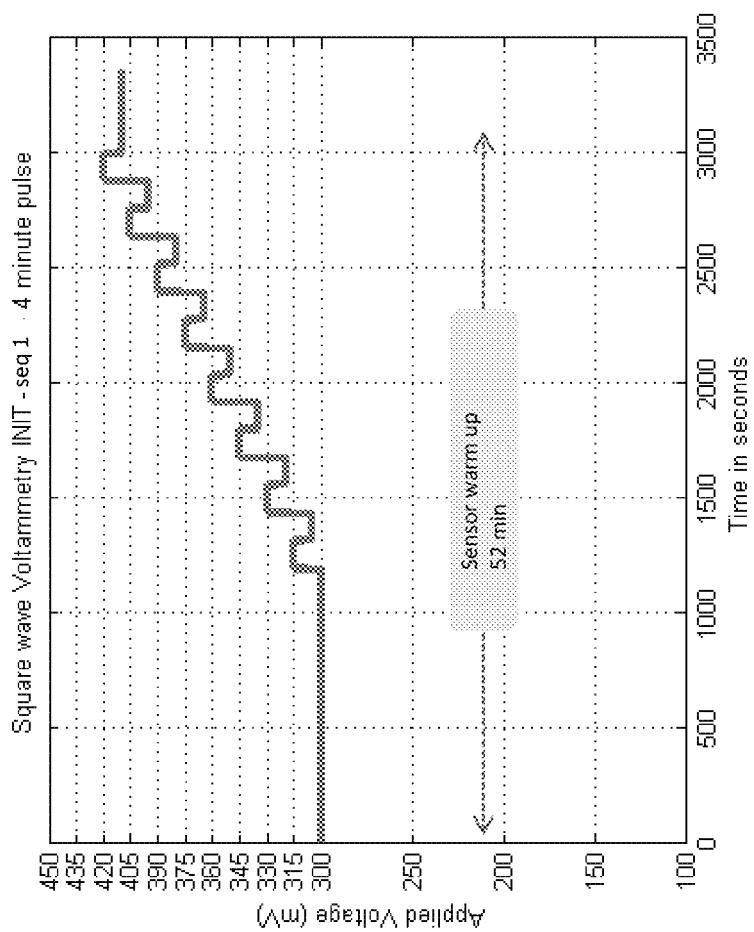
FIG. 6 illustrates an input voltage sequence applied to a Harmony 1 sensor, according to a first example.
Figure 7A:
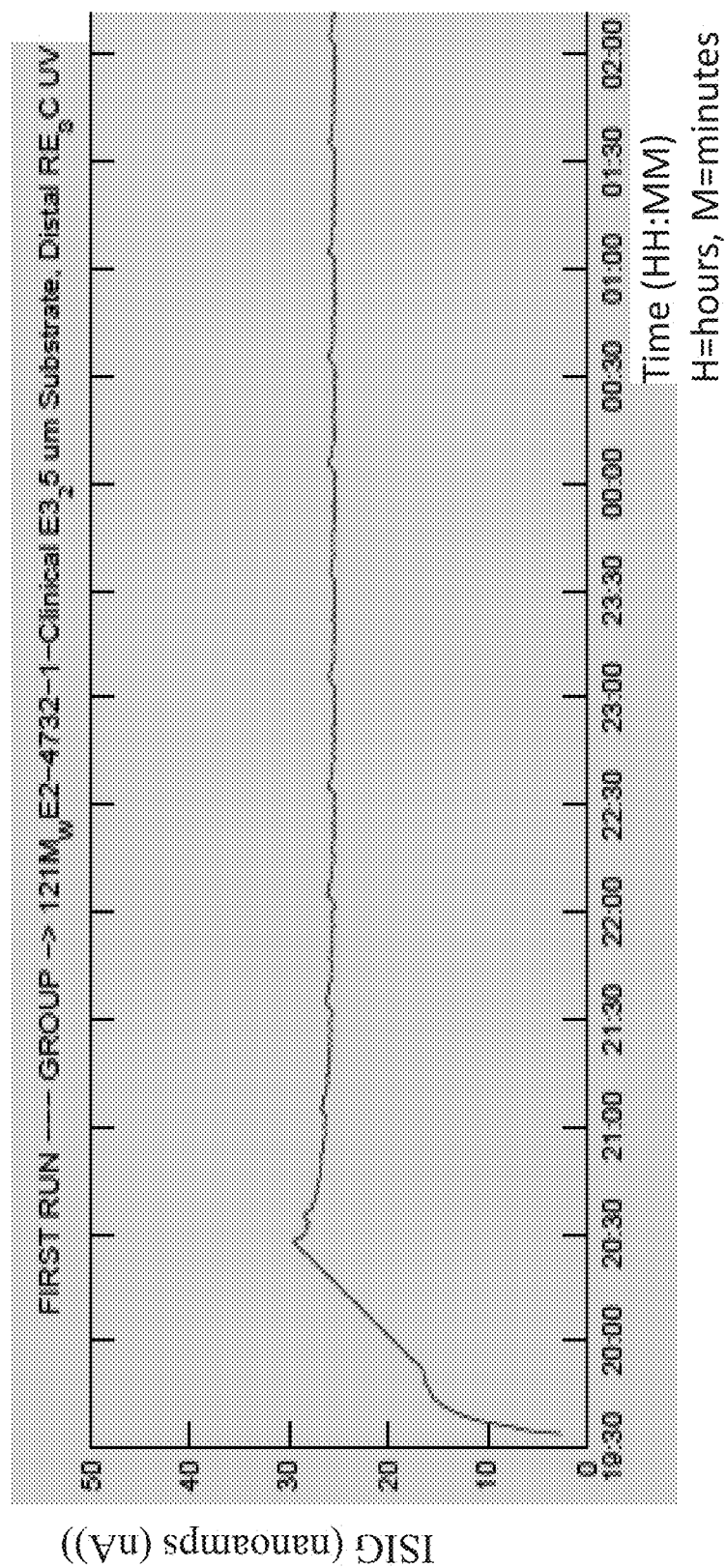
FIGS. 7A-7D plot ISIG as a function of time for a plurality of runs after application of the input voltage sequence of FIG. 6.
Figure 7B:
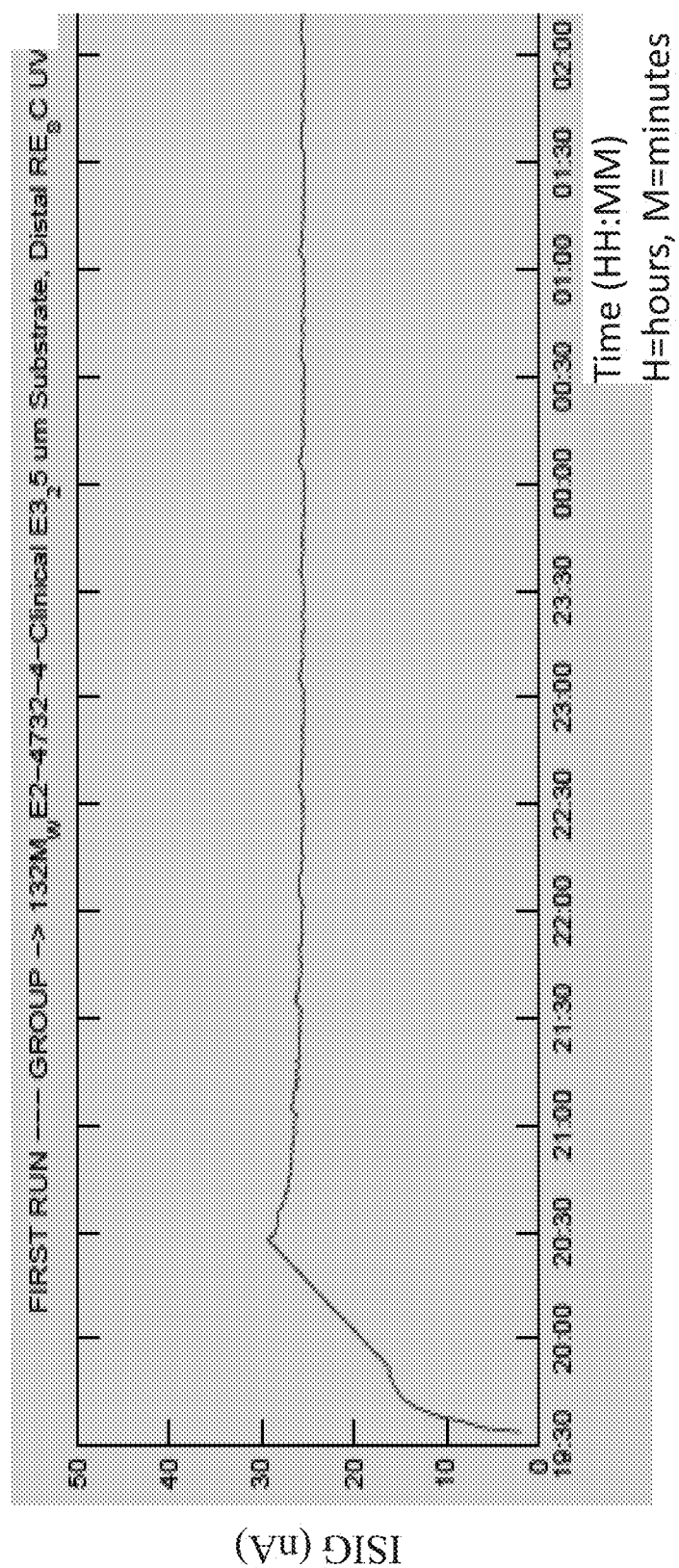
Figure 7C:
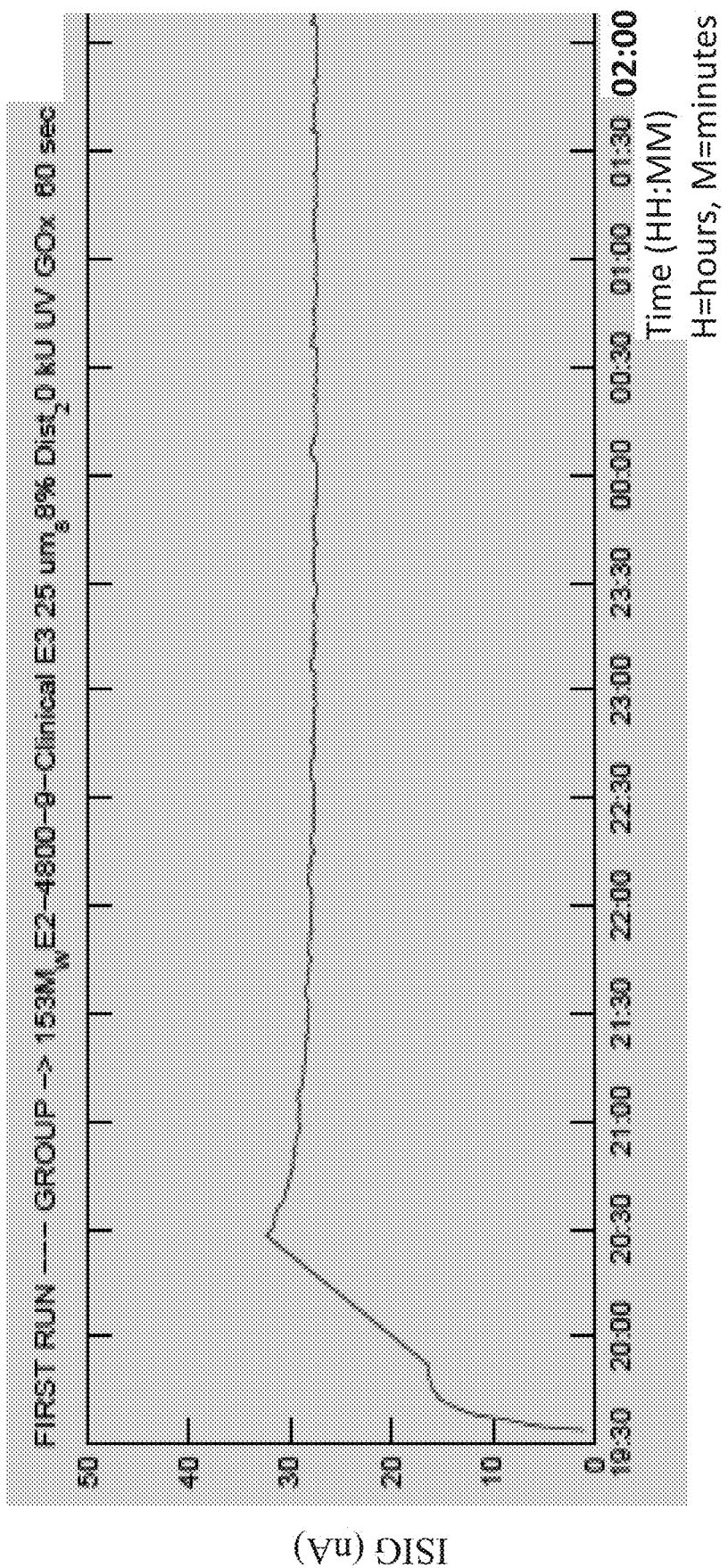
Figure 7D:
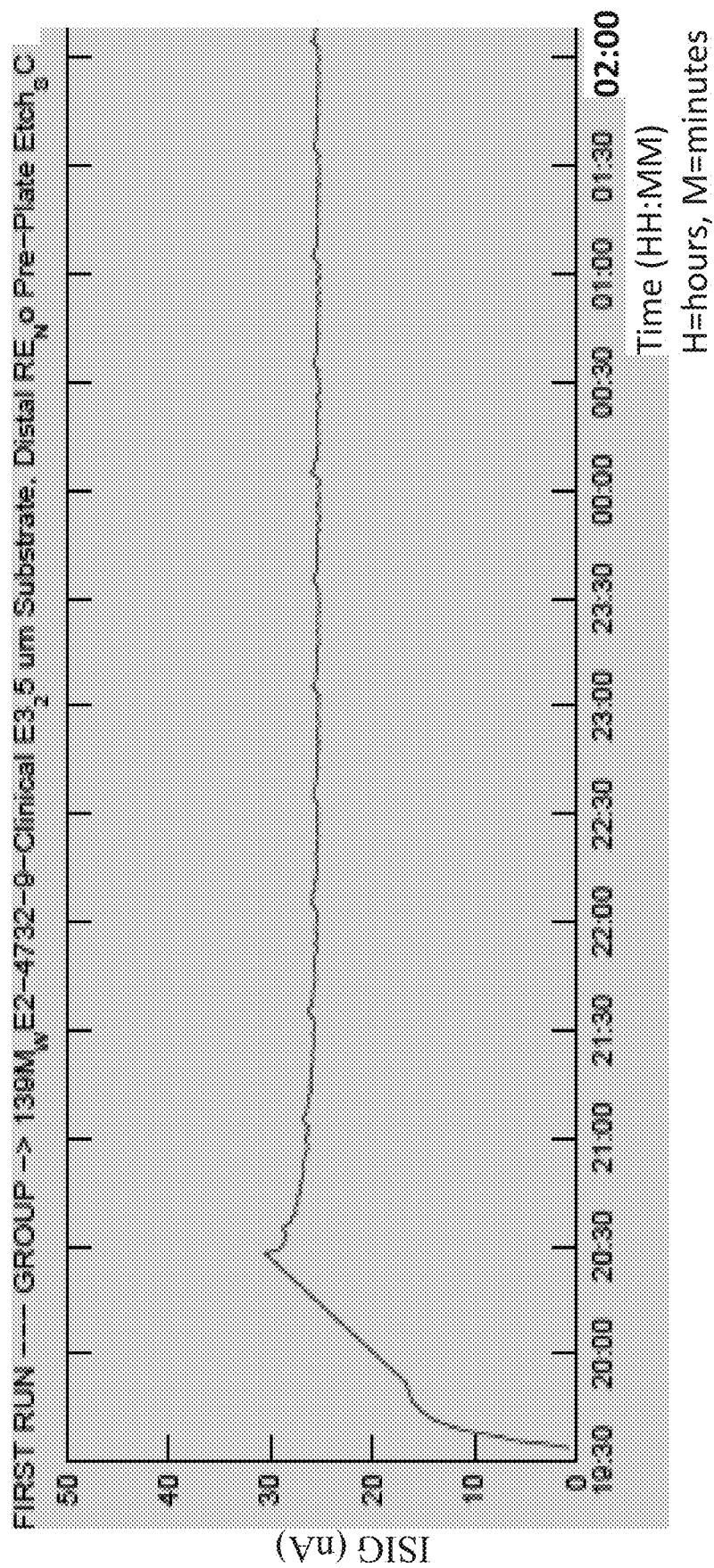

FIG. 6 illustrates a first input voltage sequence comprising a biphasic pulse ramp superimposed on a staircase voltage. The biphasic pulse period is 4 minutes.

Table 2 tabulates the parameters of the first input voltage sequence.

TABLE 2

| Sequence 1 | |
|---|---|
| Sequence 1 | |
| V initial (mV) | 300 |
| Quiet Time @ V initial (sec) | 1200 |
| V final (mV) | 410 |
| Step E (mV) | 5 |
| Pulse amplitude (mV) | 10 |
| Pulse Frequency (1/sec) | 1/240 |
| Total Warmup/Initialization Time (sec) | 3120 (52 min) |

FIGS. 7A-7D plot the output (ISIG) from the sensor after application of the first input sequence. The data shows the resulting reduction in the startup time characterized by:
Time to reach in vitro stability: 62 minutes.
Time taken to achieve in vitro run-in: 55 minutes (measured just 3 minutes after the initialization sequence ended).
Total time for which the initialization voltage was applied to achieve sensor warm up: 52 minutes.
The results are tabulated in Table 3.

TABLE 3

| FILENAME | Run-in time (minutes) | Run-in ISIG (nA) | First Stable Point (min) | First Stable ISIG (nA) |
|---|---|---|---|---|
| 121M_WE2 | 55.00 | 28.84 | 59.00 | 27.95 |
| 132M_WE2 | 54.00 | 29.33 | 62.00 | 28.11 |
| 139M_WE2 | 55.00 | 29.22 | 63.00 | 27.9 |
| 153M_WE2 | 56.00 | 31.71 | 67.00 | 30.39 |
| Mean | 55 | 29.775 | 62.75 | 28.5875 |

2. Second Input Voltage Sequence Example (Harmony 1 Sensor)

Figure 8:
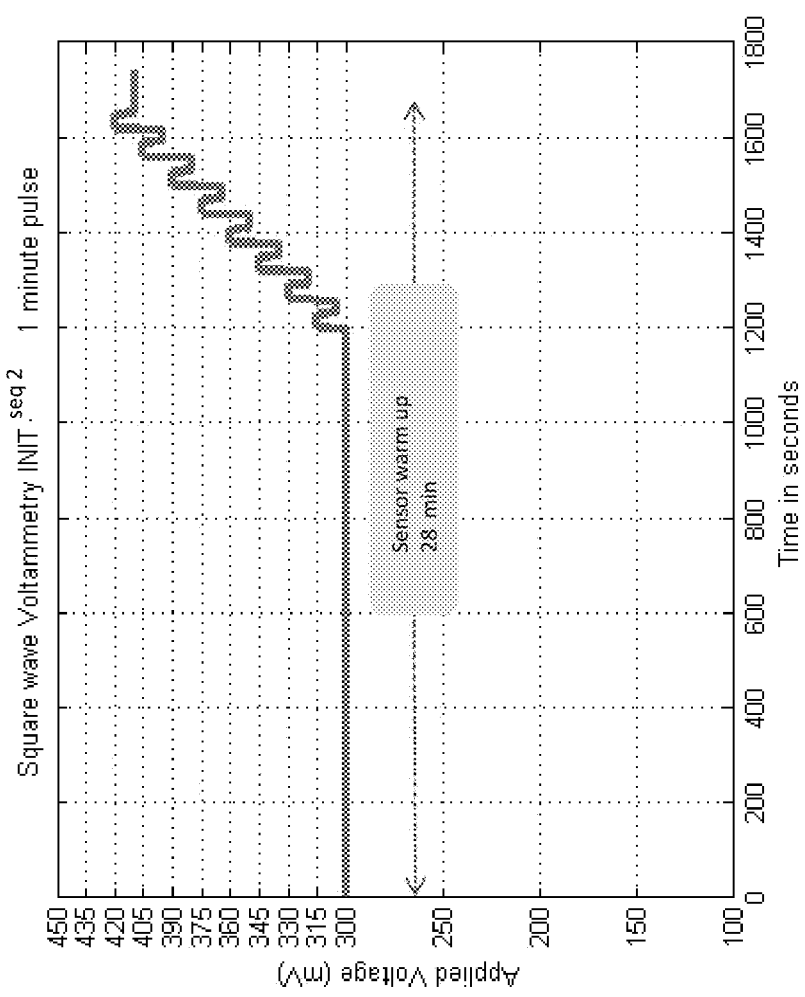
FIG. 8 illustrates an input voltage sequence applied to a Harmony 1 sensor, according to a second example.

FIG. 8 illustrates a second input voltage sequence comprising a biphasic pulse ramp superimposed on a staircase voltage. The biphasic pulse period is 1 minute. Table 4 tabulates the parameters of the second input voltage sequence.

TABLE 4

| Sequence 2 | |
|---|---|
| V initial (mV) | 300 |
| Quiet Time @ V initial (sec) | 1200 |
| V final (mV) | 410 |
| Step E (mV) | 5 |
| Pulse amplitude (mV) | 10 |
| Pulse Frequency (1/sec) | 1/60 |
| Total Warmup/Initialization Time (sec) | 1680 (28 min) |

Figure 9A:
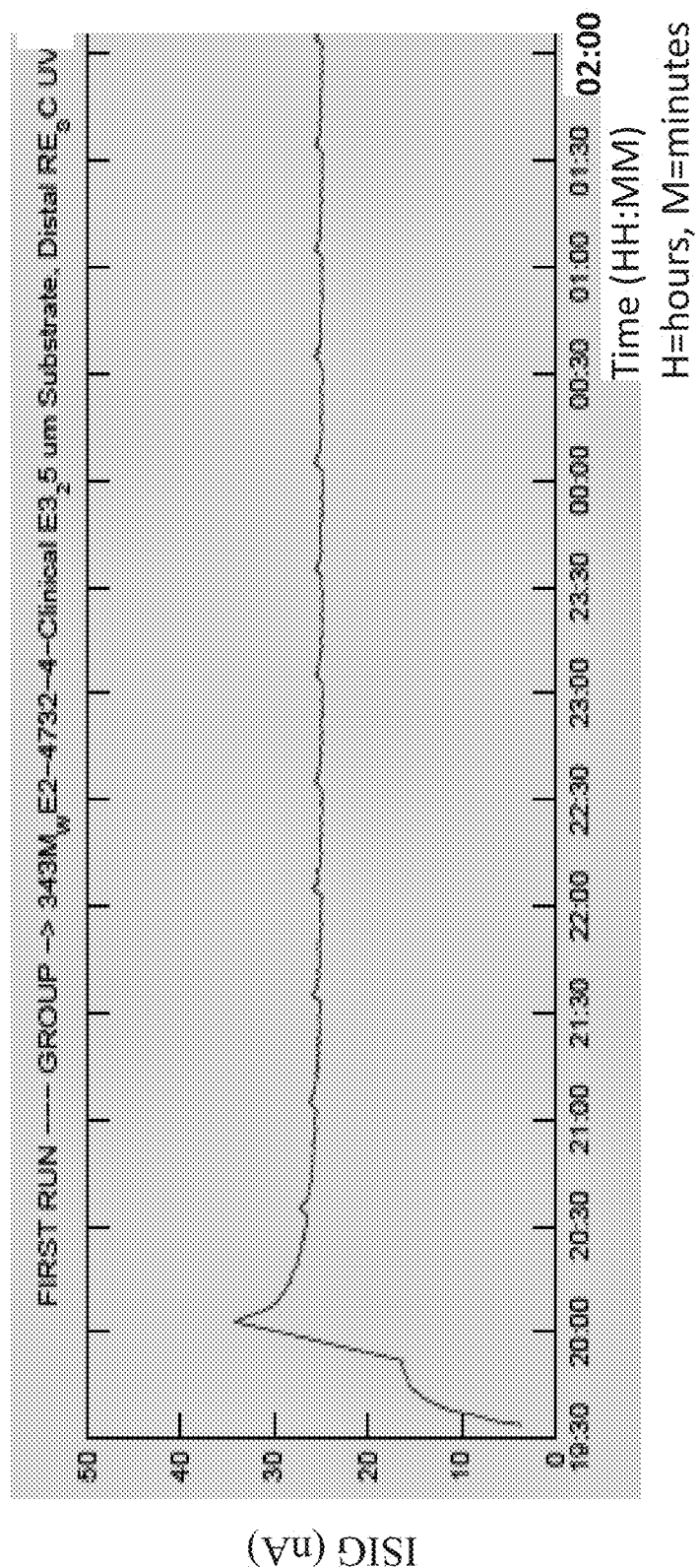
FIGS. 9A-9C plot ISIG as a function of time for a plurality of runs after application of the input voltage sequence of FIG. 8.
Figure 9B:
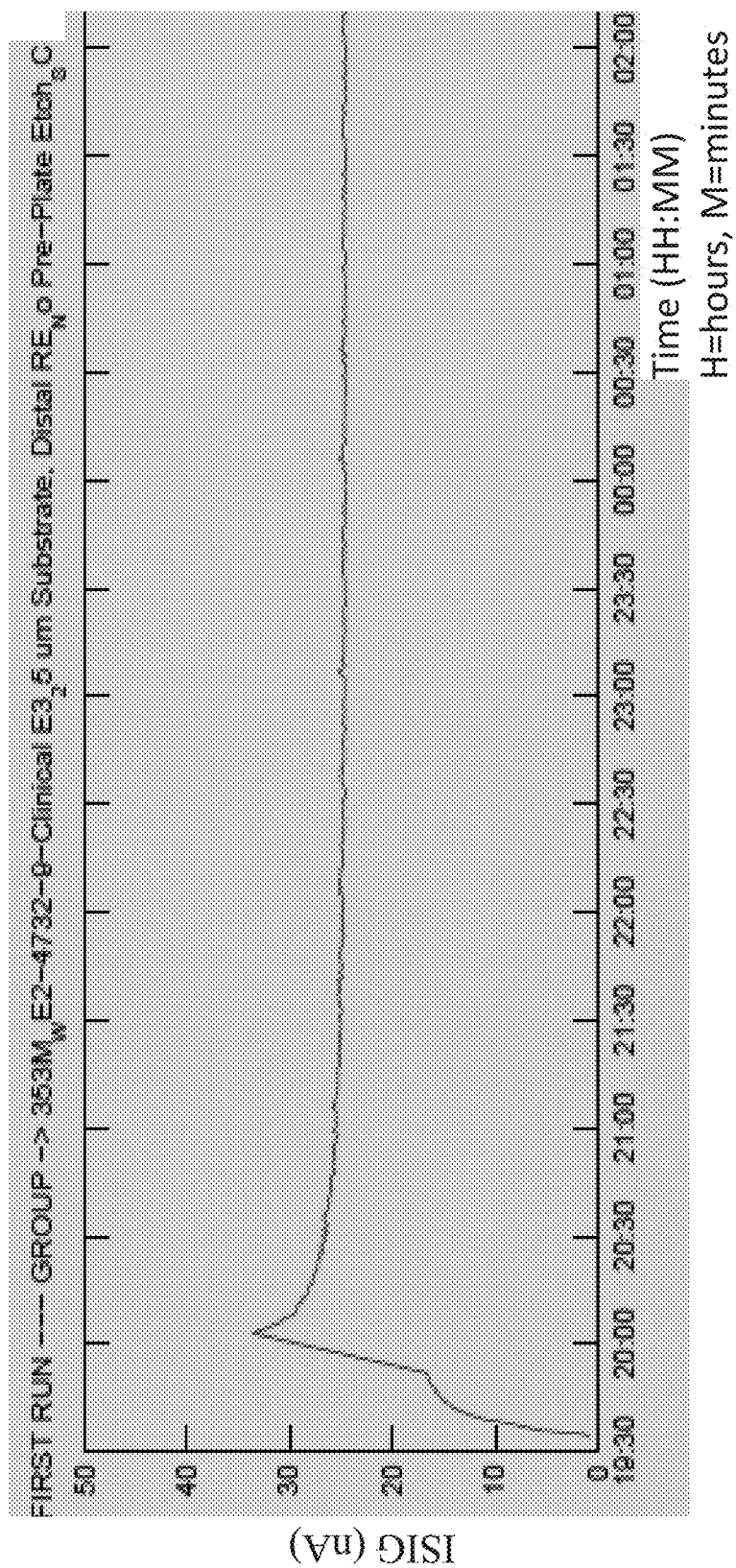
Figure 9C:
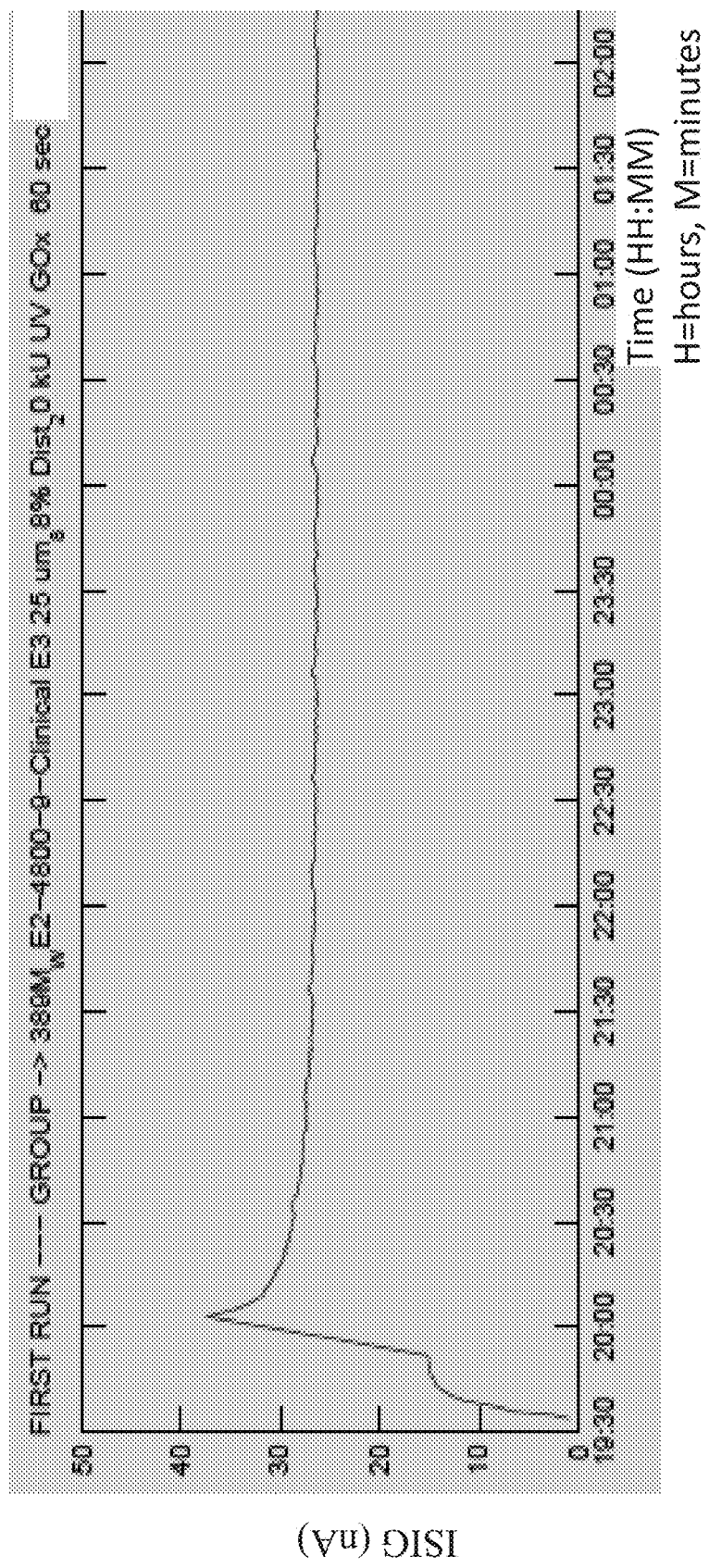

FIGS. 9A-9C plot the output (ISIG) from the sensor after application of the second input sequence. The data shows reduction in the startup time characterized by:
Time to in vitro stability: 50 minutes
Time taken to achieve in vitro run-in: 55 minutes (measured just 3 minutes after the initialization sequence ended).
Total time for which the initialization voltage was applied to achieve sensor warm up: 52 minutes.

The results are tabulated in Table 5.

TABLE 5

| FILENAME | Run-in time (minutes) | Run-in ISIG (nA) | First Stable Point (min) | First Stable ISIG (nA) |
|---|---|---|---|---|
| 343M_WE2 | 38.00 | 28.69 | 46.00 | 27.39 |
| 353M_WE2 | 40.00 | 28.22 | 50.00 | 26.97 |
| 389M_WE2 | 43.00 | 30.15 | 52.00 | 28.99 |
| Mean | 40.33 | 29.02 | 49.33 | 27.78 |

The data in the above described examples show that implementation of the initialization scheme, comprising a biphasic pulse combined with a staircase voltage, results in a surprising improvement in sensor figures of merit including a time to stability of 40-60-minutes (at least 5 times faster than the 5 hours measured for sensor without initialization, as described in FIG. 1 and the related text).

3. Third Example (Optimizing the Voltages Applied in the Initialization Protocol)

Two types of staircase initialization voltage schemes (scheme 1 and scheme 2) were implemented (see Table 6 below) on Enlite 3 sensors in a Medtronic iPro2 system, so as to understand the electrode state during initialization. Five (5) Enlite 3 sensors were tested for each scheme (details shown in Tables 7 and 8).

Figure 11:
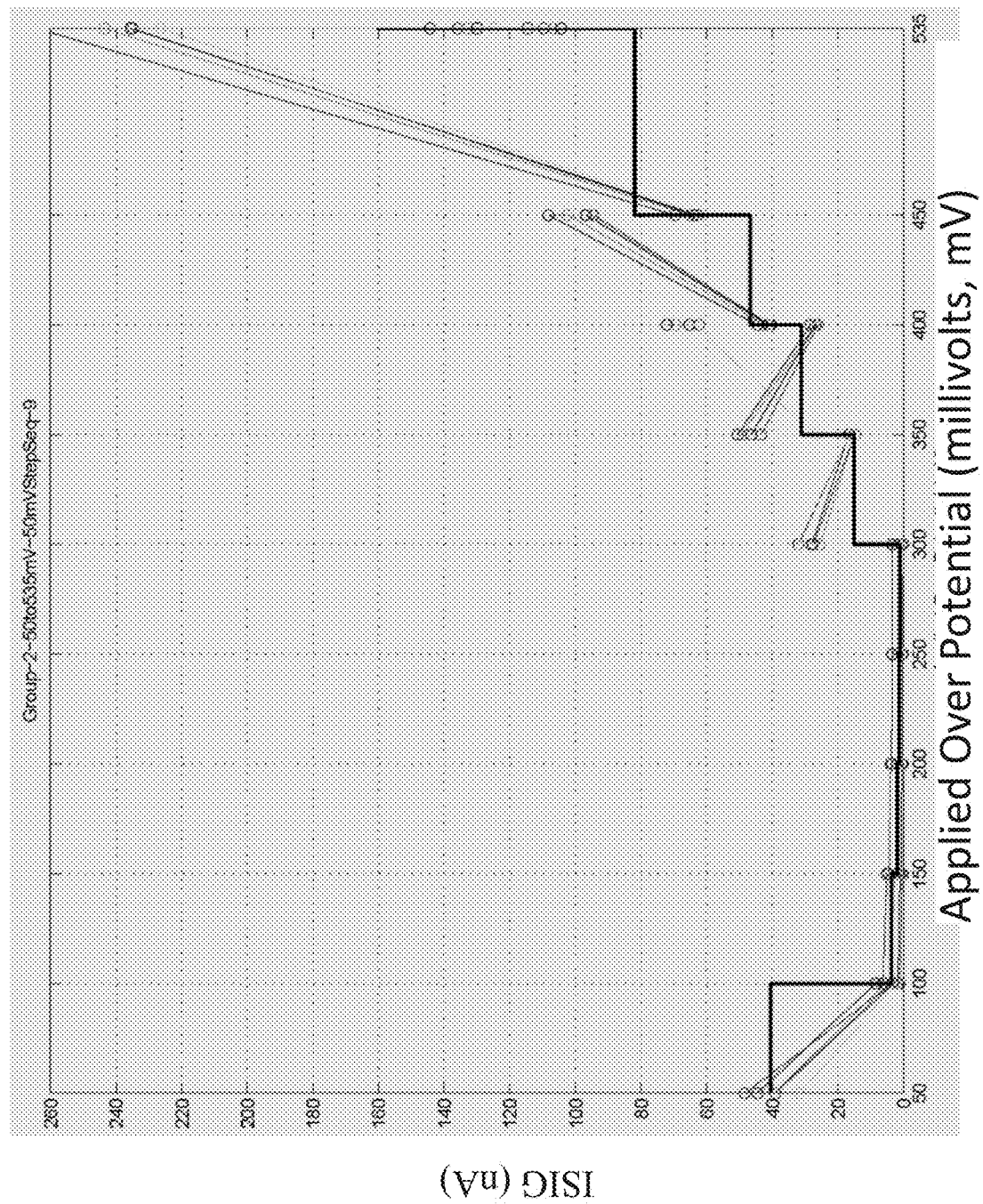
FIG. 11 plots ISIG signal versus applied voltage for scheme 2 applied to an Enlite sensor.

The output signals (ISIG) recorded during application of the staircase voltage were plotted as a function of the applied potential. The ISIG recording frequency was 1 scan per minute. Each voltage step was applied for 2 minutes so that 2 ISIG data points were collected at each voltage step (with the exception that in scheme 1, the first step of 300 mV was applied for 30 minutes). The ISIG connecting line between step voltages is always plotted from last ISIG captured at a given voltage step to the first ISIG capture at the next voltage step (see FIG. 11).

TABLE 6

Staircase Voltage INIT schemes overview

| Scheme | Start Voltage (mV) | Time at Start Voltage (min) | End Voltage (mV) | Step Size (mV) | Time per step (min) |
|---|---|---|---|---|---|
| 1 | 300 | 30 | 535 | 30 | 2 |
| 2 | 50 | 2 | 535 | 50 | 2 |

TABLE 7

Staircase scheme 1 - 300 mV to 535 mV
Scheme 2 - 300 mV to 535 mV

| Step | Voltage (mV) | Step Size (mV) | Step Duration (min) |
|---|---|---|---|
| 1 | 300 | 0 | 30 |
| 2 | 330 | 30 | 2 |
| 3 | 360 | 30 | 2 |
| 4 | 390 | 30 | 2 |
| 5 | 420 | 30 | 2 |
| 6 | 450 | 30 | 2 |
| 7 | 480 | 30 | 2 |
| 8 | 510 | 30 | 2 |
| 9 | 535 | 25 | 2 |

TABLE 8

Staircase scheme 3 - 50 mV to 535 mV
Scheme 2 - 50 mV to 535 mV

| Step | Voltage (mV) | Step Size (mV) | Step Duration (min) | ISIG (nA) |
|---|---|---|---|---|
| 1 | 50 | 0 | 30 | |
| 2 | 100 | 50 | 2 | |
| 3 | 150 | 50 | 2 | |
| 4 | 200 | 50 | 2 | |
| 5 | 250 | 50 | 2 | |
| 6 | 300 | 50 | 2 | |
| 7 | 350 | 50 | 2 | |
| 8 | 400 | 50 | 2 | |
| 9 | 450 | 50 | 2 | |
| 10 | 535 | 85 | 2 | | a. Scheme 1

Figure 10:
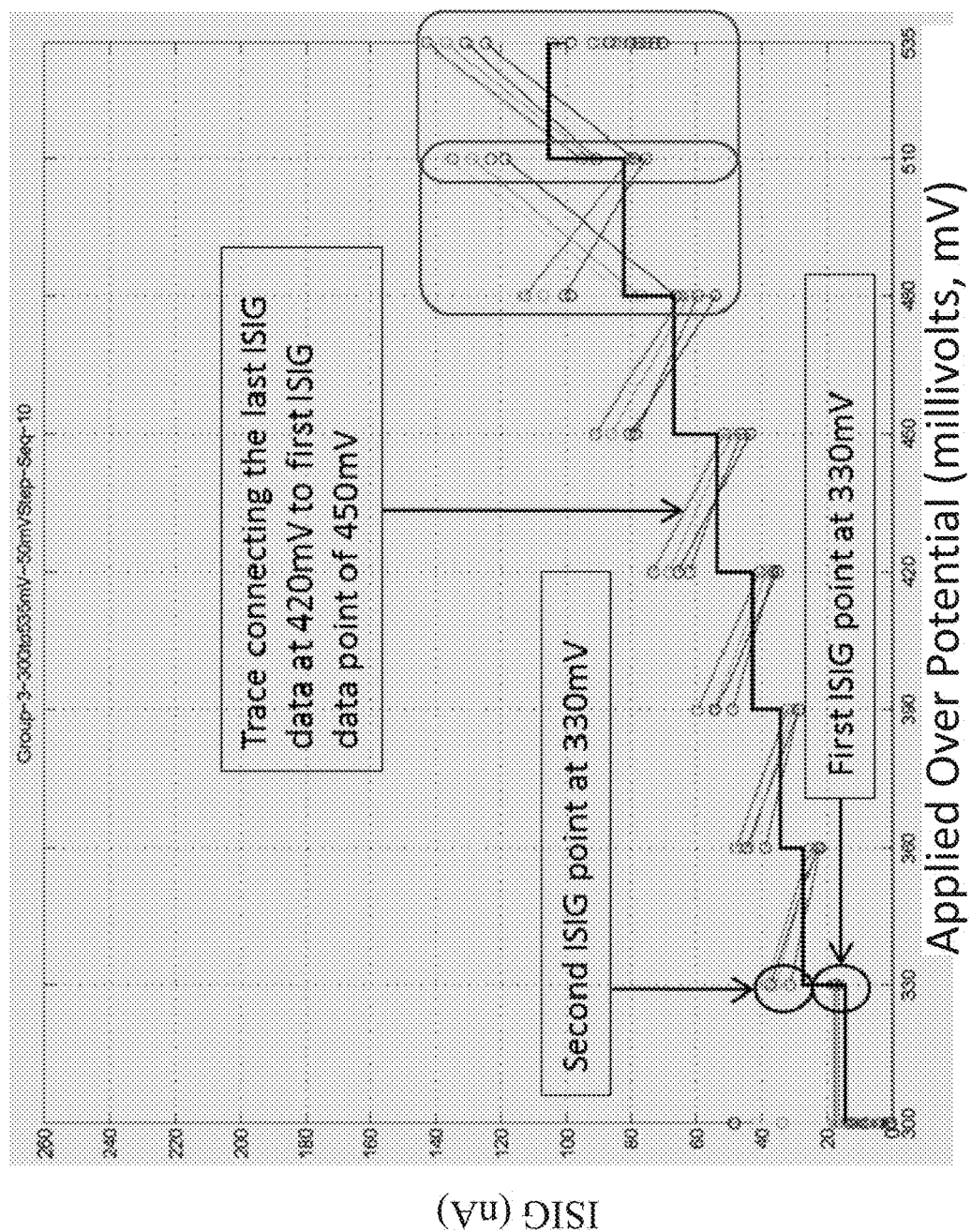
FIG. 10 plots ISIG signal versus applied voltage for scheme 1 applied to an Enlite sensor.

FIG. 10 shows the ISIG versus applied voltage for scheme 1.

The recorded data for this scheme shows that, for voltage steps from 300 mV through 480 mV, the ISIG did not exhibit any charging or faradaic current characteristics, i.e. the first ISIG point at any given voltage is always lower than the second ISIG data point collected at that voltage (see FIG. 10).

For 3 out of 5 sensors tested (grey, black and green trace in FIG. 10), the charging and the faradaic currents are first manifested for a voltage jump from 480 mV to 510 mV, i.e. the second ISIG data point collected has decayed and is lower than the first ISIG data point collected. For voltage steps from 510 mV to 535 mV, all the sensors output charging and faradaic currents.

b. Scheme 2

The plotted results for scheme 2 (voltage step from 0 mV through 300 mV) do not show any significant collected ISIG and most of the time ISIG stayed low and near 0 nA.

For 1 out of 5 sensors tested (grey trace in FIG. 11), the charging and the faradaic currents are first manifested for a voltage jump from 350 mV to 400 mV, i.e. the second ISIG data point collected has decayed and is lower than the first ISIG data point collected.

For voltage steps from 400 mV to 450 mV and from 450 mV to 535 mV, all the sensors outputted charging and faradaic current.

The data for two above schemes shows that the initial manifestation of charging and the faradic currents, and the magnitude of these currents, depend on the magnitude of the voltage and the voltage step size. Origination of these charging and faradaic current can be pushed right towards the operating potential of 535 mV when the step sizes are small. In addition, the ISIG magnitudes are smaller for scheme 2 compared to scheme 1, and thus voltage step size can be used to change the state of the platinum in the electrode in a much softer fashion without damaging the platinum surface.

Advantages and Improvements

As described herein, illustrative embodiments of the initialization schemes may provide the following advantages:

1. The sensor initialization scheme can be tailored so that high and damaging current is not passed through the sensor electrode. Lower ISIG current generation during the initialization phase reduces undesirable chrome loss from the sensor.

2. Each sensor can have an adaptive initialization more suited to its individual plating and chemically active layers.

3. Since the sensor initialization depends on the environment in which the sensor is operated (ionic strength), the Vset applied to the potentiostat may be selected from a pre-determined range to achieve initialization more suited to specific in-vivo environments (depending on the individual sensor and the environment in which the sensor is operated).

4. Harmony 1 sensor uses 400 mV operating potential without implementation of any sensor initialization scheme. This no initialization approach in turn can lead to higher background current, significantly impacting day 1 ISIG performance (as characterized by a high background current) and consequently also negatively impacting in-vivo performance of the sensor. As a result, custom calibration algorithms need to be developed and implemented for day 1. Illustrative embodiments of the initialization protocol described herein, on the other hand, reduce damage to the sensor and help with faster sensor run in (lower background) so that specialized calibration algorithms do not need to be implemented for day 1, thereby improving day 1 sensor performance.

Process Steps

FIG. 12 illustrates a method of making and/or initializing a sensor. The method provides a technique to differentiate between voltages that drive non-faradaic/charging current (due to charge redistribution across the sensor) and voltages that drive faradaic current (due to reactions involving various species of redox couples).

The method comprises the following steps.

Block 1200 represents providing a sensor. In one or more embodiments, the sensor comprises a base substrate; a working electrode comprising metal having an electroactive surface, the working electrode disposed on the base substrate; an analyte sensing layer disposed over the working electrode, the analyte sensing layer detectably altering the electrical current at the electrode in the presence of an analyte; and an analyte modulating layer disposed over the analyte sensing layer, wherein the analyte modulating layer modulates diffusion of the analyte therethrough.

Examples of sensors include, but are not limited to, an Enlite 3 GM sensor, an Enlite 3 670G sensor, a Harmony 1 sensor, or a Harmony 2 sensor as manufactured by Medtronic™.

Block 1202 represents connecting a circuit to the sensor. The circuit generates and transmits an initialization voltage to the electrode, wherein the initialization voltage comprises a ramped voltage (e.g., staircase or stepped voltage) combined with a biphasic voltage pulse.

In one or more examples, the circuit comprises a potentiostat (e.g., as illustrated in FIG. 5) connected to a voltage generation circuit 1400. The voltage generation circuit generates and inputs the initialization voltage (Vset) to the potentiostat and the potentiostat transmits the initialization voltage to the electrode and the electroactive surface.

In various examples, the ramped voltage is applied for a variety of voltage step sizes and sweep rates, and/or EIS is performed at various frequencies so as to identify the properties of the voltage ramp that improve sensor startup. Thus, the voltammetry can be used to determine a range of operating potentials (Vset) at which the sensor may be initialized (as evidenced by manifestation of charging and faradaic currents). The Vset range may be different for different configurations of the sensor.

Block 1204 represents using the circuit (e.g., an ammeter A as illustrated in FIG. 5) to measure the electrical current (e.g., ISIG) as a function of voltage in the ramped voltage. In one example, the measuring comprises, for each of a plurality of the voltages in the ramped voltage, measuring the electrical current at a first time and at a later second time.

Block 1206 represents determining, in a computer 1400 or special purpose processor, a voltage reference level that can be used to start the initialization process. In illustrative embodiments, the computer or special purpose processor determines the threshold voltage in the ramped voltage at and above which the electrical current is faradaic. In one example, the determining comprises comparing the electrical current at the two different times (the first time and the second time); and selecting the threshold voltage as the lowest voltage in the voltage ramp for which the electrical current measured at the first time is higher than the electrical current measured at the second time (see e.g., FIGS. 10 and 11).

Block 1208 represents applying an initialization voltage to the electroactive surface, wherein the initial voltage (Vset) is at least equal to, or within 5% of, the threshold voltage determined in Block 1206. In various examples, the voltage generation circuit adjusts a voltage step in the ramped voltage so that the ramped voltage is ramped from the initial voltage to the final voltage in less than 1 hour. In one or more embodiments, the initialization scheme comprises the voltage sequence described in FIG. 13.

Block 1210 represents the end result, a sensor wherein the metal in the working electrode has a stable charge distribution. In one or more embodiments, the sensor is characterized by having an ISIG in 5% agreement with a 2 hr moving average and in 10% agreement with a stable (e.g., steady state) ISIG. This strict in-vitro criteria has been defined for quantification of the sensor performance as well as for comparison of the sensor performance using the novel initialization scheme(s) described herein with the sensor performance without any initialization.

The process described in reference to FIG. 12 provides a platform for improved intelligent and adaptive sensor initialization. This adaptive initialization is capable of tailoring the initialization process to account for physiological differences (patient to patient variability) and manufacturing variability (sensor to sensor variability due to variations in the electrode and other chemically active layers). Thus, the present invention provides initialization schemes that transform the physical and/or chemical properties of various layers (electrodes and/or other chemically active layers) in the sensor, so as to achieve a sensor having improved performance with faster start up times (faster time to stable or steady state operation).

Figure 13:
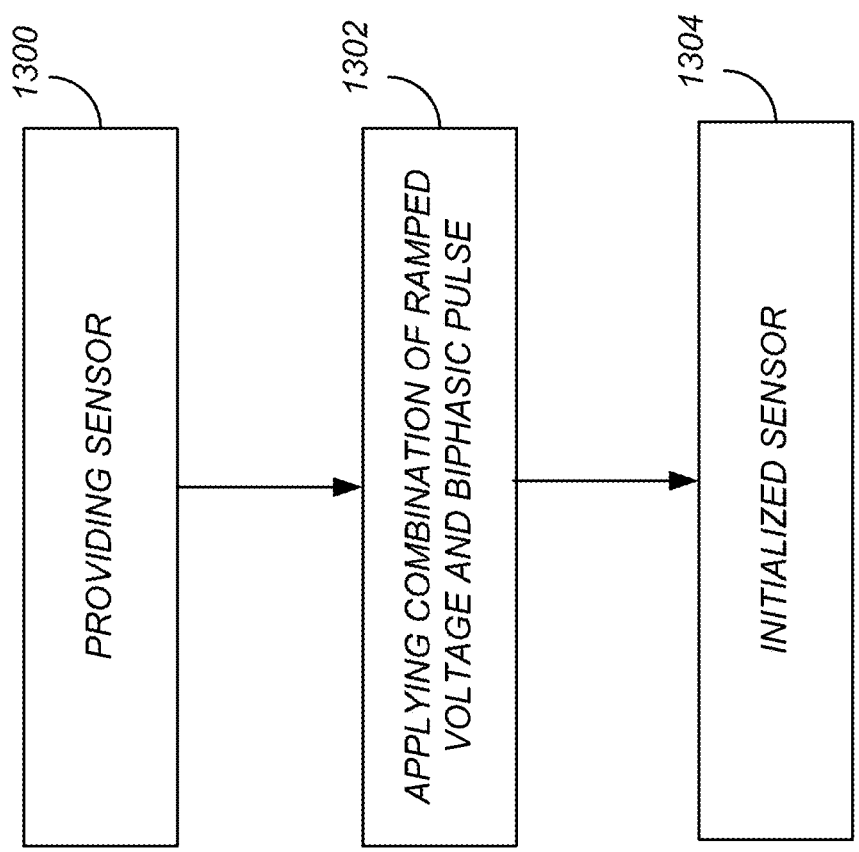
FIG. 13 is a flowchart illustrating a method of making a sensor according to another embodiments.

FIG. 13 illustrates a method of making and/or initializing a sensor. The method comprises the following steps.

Block 1300 represents providing a sensor. In one or more embodiments, the sensor comprises a base substrate; a working electrode comprising metal having an electroactive surface, the working electrode disposed on the base substrate; an analyte sensing layer disposed over the working electrode, the analyte sensing layer detectably altering the electrical current at the electrode in the presence of an analyte; and an analyte modulating layer disposed over the analyte sensing layer, wherein the analyte modulating layer modulates diffusion of the analyte therethrough.

Block 1302 represents connecting a circuit to the sensor. The circuit generates and transmits an initialization voltage to the electrode, and the initialization voltage comprises a ramped voltage (e.g., staircase or stepped voltage) combined with a biphasic voltage pulse (e.g., having a frequency in a range of 0.1 Hz to 8 kHz). In one example, the initialization starts at the leading edge of the faradaic operation regime (~300 mV) and continues by applying a potential that superimposes the biphasic voltage pulse over the ramped voltage.

In one or more embodiments, in order to speed up the initialization process, a non glucose overpotential (e.g., a voltage pulse in a range of 0-200 mV) is applied in the quiet time.

In one or more examples, the circuit comprises a potentiostat (e.g., as illustrated in FIG. 5) connected to a voltage generation circuit 1400. The voltage generation circuit generates and inputs the initialization voltage (Vset) to the potentiostat and the potentiostat transmits the initialization voltage to the electrode and the electroactive surface.

In one or more embodiments, the ramped voltage comprises a voltage stepped from an initial voltage, causing charge re-distribution in the electrode or starting at the leading edge of a faradaic operation regime (e.g., about 300 mV), to a final voltage at which the sensor or potentiostat is biased (e.g., Vset) when the electrical current provides a reliable measure the analyte during steady state operation. Examples of the initial voltage include, but are not limited to, voltages in a range of 250-450 mV. Examples of the final voltage include, but are not limited to, voltages in a range of 400 mV-600 mV. In one or more examples, the initial voltage is at least equal to, or within 5% of, the lowest voltage Vset inputted to the potentiostat for which the electrical current (e.g., ISIG) is faradaic.

As described herein, the voltage generation circuit may adjust a voltage step in the ramped voltage so that the ramped voltage is ramped from the initial voltage to the final voltage in less than one hour. For example, the ramped voltage may be applied for a duration and comprise voltage magnitudes below a threshold, so that metal loss from the electrode and/or the base layer is less than 1%.

Block 1304 represents the end result, a sensor comprising a working electrode comprising a metal having a stable charge distribution. In one or more embodiments, the initialization voltage changes a charge distribution of the metal in the electrode, so that after less than 1 hour from when the initialization voltage is first applied, the sensor is characterized by having an ISIG in 5% agreement with a 2 hr moving average and in 10% agreement with a stable (steady state, non-transient) ISIG.

Moreover, the adaptive or non-adaptive staircase voltage initialization (SVI) applied to the sensors described herein helps with sensor initialization without using high magnitude signal generation. High ISIG generation during the sensor initialization can be harsh on the sensor electrode and degrade sensor performance.

Processing Environment

Figure 14:
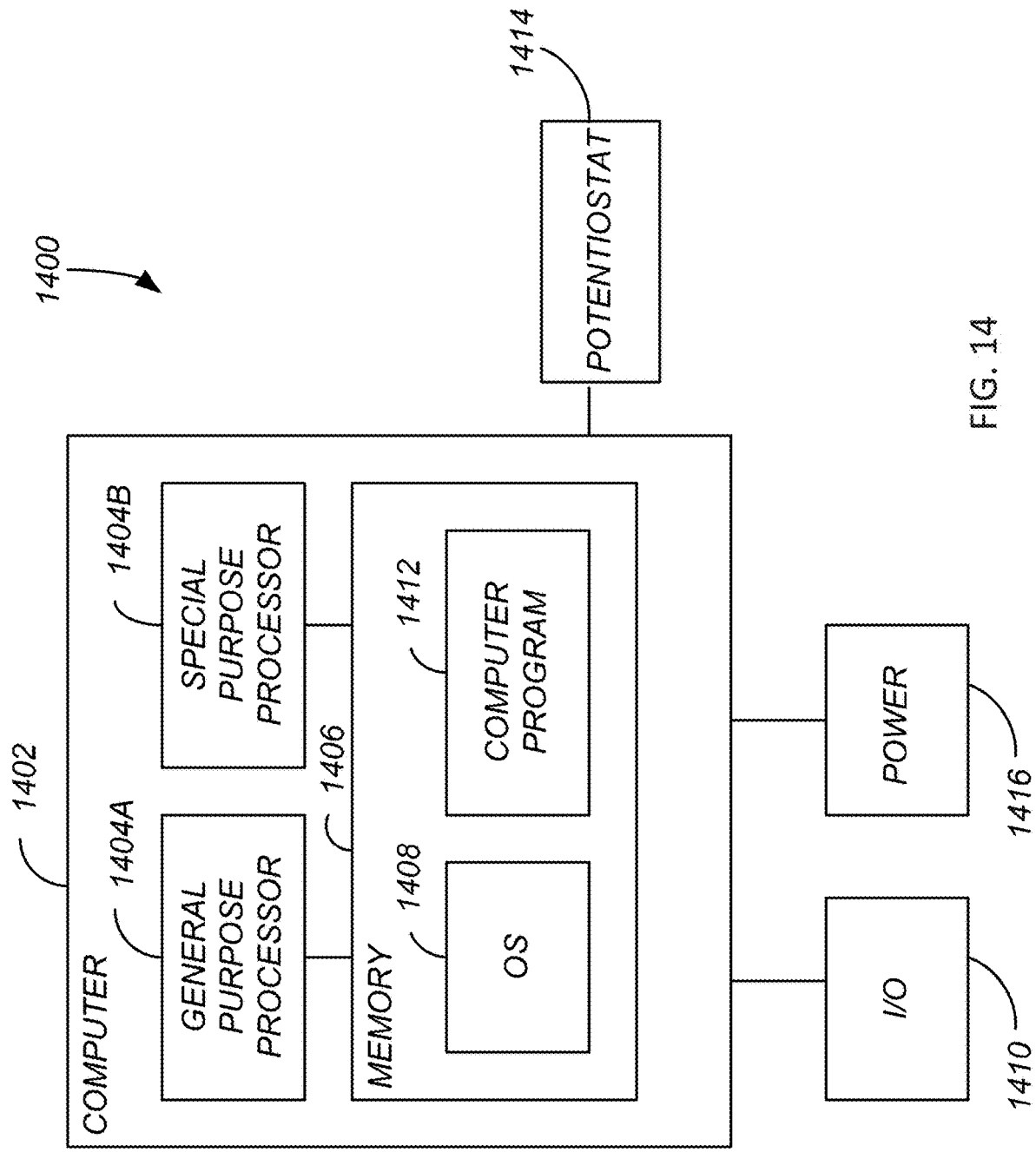
FIG. 14 illustrates a hardware environment for implementing one or more embodiments of the invention.

FIG. 14 illustrates an exemplary system 1400 that could be used to apply the initialization voltages and voltage ramps disclosed herein.

The computer 1402 comprises a processor 1404 (general purpose processor 1404A and special purpose processor 1404B) and a memory, such as random access memory (RAM) 1406. Generally, the computer 1402 operates under control of an operating system 1408 stored in the memory 1406, and interfaces with the user/other computers to accept inputs and commands (e.g., analog or digital signals) and to present results through an input/output (I/O) module 1410. The computer program application 1412 accesses and manipulates data stored in the memory 1406 of the computer 1402. The operating system 1408 and the computer program 1412 are comprised of instructions which, when read and executed by the computer 1402, cause the computer 1402 to perform the operations herein described. In one embodiment, instructions implementing the operating system 1408 and the computer program 1410 are tangibly embodied in the memory 1406, thereby making a computer program product or article of manufacture. As such, the terms "article of manufacture," "program storage device" and "computer program product" as used herein are intended to encompass a computer program accessible from any computer readable device or media.

In one embodiment, computer 1402 comprises one or more field programmable gate arrays (FPGAs) or application specific integrated circuits (ASICs).

The computer system 1400 is connected to the working electrode (e.g., via a circuit such as a potentiostat 1414) so as to apply the voltages Vset.

FIG. 14 further illustrates a power source 1416 for providing power to the system 1400.

Those skilled in the art will recognize many modifications may be made to this configuration without departing from the scope of the present disclosure. For example, those skilled in the art will recognize that any combination of the above components, or any number of different components, peripherals, and other devices, may be used.

Figure 15:
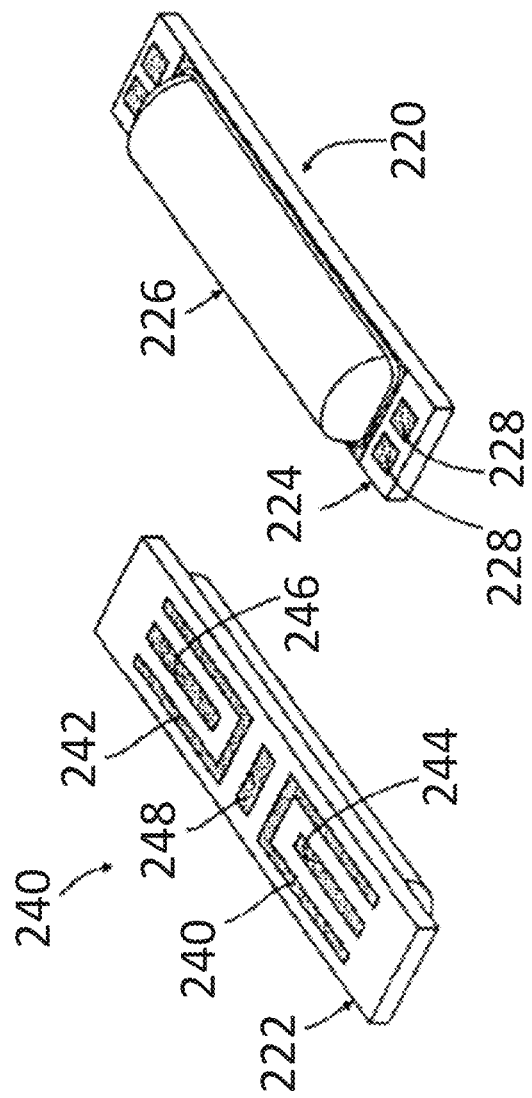
FIG. 15 illustrates implantable sensor and electronics for driving the implantable sensor according to an embodiment of the present invention.

FIG. 15 illustrates an implantable sensor and electronics for driving the implantable sensor according to an embodiment of the present invention. FIG. 15 shows a substrate 220 having two sides, a first side 222 of which contains an electrode configuration and a second side 224 of which contains electronic circuitry. As may be seen in FIG. 15, a first side 222 of the substrate comprises two counter electrode-working electrode pairs 240, 242, 244, 246 on opposite sides of a reference electrode 248. A second side 224 of the substrate comprises electronic circuitry. As shown, the electronic circuitry may be enclosed in a hermetically sealed casing 226, providing a protective housing for the electronic circuitry. This allows the sensor substrate 220 to be inserted into a vascular environment or other environment which may subject the electronic circuitry to fluids. By sealing the electronic circuitry in a hermetically sealed casing 226, the electronic circuitry may operate without risk of short circuiting by the surrounding fluids. Also shown in FIG. 15 are pads 228 to which the input and output lines of the electronic circuitry may be connected. The electronic circuitry itself may be fabricated in a variety of ways. According to an embodiment of the present invention, the electronic circuitry may be fabricated as an integrated circuit using techniques common in the industry.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

The invention claimed is:

1. An analyte sensor apparatus, comprising:
a base substrate;
an analyte sensing layer disposed over an electrode, wherein the analyte sensing layer detectably alters electrical current at the electrode in a presence of an analyte;
an analyte modulating layer disposed over the analyte sensing layer, wherein the analyte modulating layer modulates diffusion of the analyte therethrough; and
a circuit coupled to the electrode, the circuit generating and transmitting an initialization voltage to the electrode and the initialization voltage comprising a ramped voltage combined with a biphasic pulse comprising an anodic phase and a cathodic phase with respect to a reference level, wherein:
the electrode comprises a metal forming an electroactive surface of the electrode,
the initialization voltage changes a charge distribution of the metal, so that after less than 1 hour from when the initialization voltage is first applied:
the electrical current is in 5% agreement with a 2 hour moving average electrical current value, and
the electrical current is in 10% agreement with a steady state (non-transient) electrical current.

2. The sensor of claim 1, wherein the ramped voltage comprises a staircase voltage.

3. The sensor of claim 1, wherein:
the circuit comprises a potentiostat connected to a voltage generation circuit,
the voltage generation circuit generates and inputs the initialization voltage to the potentiostat,
the potentiostat transmits the initialization voltage to the electrode, and
the ramped voltage comprises a voltage stepped from an initial voltage, causing charge re-distribution in the electrode, to a final voltage at which the potentiostat is biased when the electrical current provides a reliable measure of the analyte concentration during steady state operation.

4. The sensor of claim 3, wherein the initial voltage is in a range of 250-450 mV and the final voltage is in a range of 400 mV-600 mV.

5. The sensor of claim 3, wherein the initial voltage is at least equal to, or within 5% of, the lowest voltage inputted to the potentiostat for which the electrical current is faradaic.

6. The sensor of claim 5, wherein the voltage generation circuit adjusts a voltage step in the ramped voltage so that the ramped voltage is ramped in less than 1 hour from the initial voltage to the final voltage.

7. The sensor of claim 1, wherein the biphasic pulse has a frequency in a range of 0.1 Hz to 8 kHz.

8. The sensor of claim 1, wherein the ramped voltage is applied for a duration and comprises voltage magnitudes below a threshold, so that metal loss from the electrode and/or the base layer is less than 1%.

9. A method of making a sensor, comprising:
connecting a circuit to a working electrode in a sensor comprising:
 a base substrate;
 the working electrode on the base substrate, wherein the working electrode comprises metal having an electroactive surface;
 an analyte sensing layer disposed over the working electrode, wherein the analyte sensing layer detectably alters electrical current at the working electrode in a presence of an analyte; and
 wherein:
 the circuit generates and transmits an initialization voltage to the working electrode, the initialization voltage comprising a ramped voltage combined with a biphasic pulse so as to form the metal having a stable (steady state) charge distribution, the biphasic pulse comprising an anodic phase and a cathodic phase with respect to a reference level, and
 the initialization voltage changes a charge distribution of the metal, so that after less than 1 hour from when the initialization voltage is first applied:
 the electrical current is in 5% agreement with a 2 hour moving average electrical current value, and
 the electrical current is in 10% agreement with a steady state (non-transient) electrical current.

10. The method of claim 9, wherein the ramped voltage comprises a staircase voltage.

11. A method of making a sensor, comprising:
connecting a circuit to a working electrode in a sensor comprising:
 a base substrate;
 the working electrode on the base substrate, wherein the working electrode comprises metal having an electroactive surface;
 an analyte sensing layer disposed over the working electrode, wherein the analyte sensing layer detectably alters electrical current at the working electrode in a presence of an analyte; and
 wherein:
 the circuit generates and transmits an initialization voltage to the working electrode, the initialization voltage comprising a first ramped voltage combined with a biphasic pulse so as to form the metal having a stable (steady state) charge distribution, the biphasic pulse comprising an anodic phase and a cathodic phase with respect to a reference level,
 the circuit comprises a potentiostat connected to a voltage generation circuit,
 the voltage generation circuit generates and inputs the initialization voltage to the potentiostat,
 the potentiostat transmits the initialization voltage to the electrode,
 the first ramped voltage comprises a voltage stepped from an initial voltage, causing charge re-distribution in the electrode, to a final voltage at which the sensor is biased when the electrical current provides a reliable measure the analyte during steady state operation, and
 the circuit generates and transmits a second ramped voltage to the electroactive surface, the method further comprising:
 measuring the electrical current as a function of the second ramped voltage;
 determining, in a computer, the threshold voltage in the second ramped voltage at and above which the electrical current is faradaic; and
 generating the initialization voltage, wherein the initial voltage is at least equal to, or within 5% of, the threshold voltage.

12. The method of claim 11, wherein the initial voltage is in a range of 250-450 mV and the final voltage is in a range of 400-600 mV.

13. The method of claim 11, wherein the biphasic pulse has a frequency in a range of 0.1 Hz to 8 kHz.

14. The method of claim 11, further comprising adjusting a voltage step in the ramped voltage so that the ramped voltage is ramped in less than 1 hour from the initial voltage to the final voltage.

15. The method of claim 11, wherein:
the measuring comprises, for each of a plurality of the voltages in the second ramped voltage, measuring the electrical current at a first time and a second time later than the first time, and
the determining comprises:
comparing the electrical current at the first time and the second time; and
selecting the threshold voltage as the lowest voltage in the voltage ramp for which the electrical current measured at the first time is higher than the electrical current measured at the second time.

16. A method of making a sensor comprising:
connecting a circuit to a working electrode in a sensor comprising:
 a base substrate;
 the working electrode disposed on the base substrate, the working electrode comprising a metal having an electroactive surface;
 an analyte sensing layer disposed over the working electrode, wherein:
 the analyte sensing layer detectably alters an electrical current at the working electrode in the presence of an analyte, and
 the circuit generates and transmits a ramped voltage to the electroactive surface,
measuring the electrical current as a function of the ramped voltage, wherein the measuring comprises, for each of a plurality of the voltages in the ramped voltage, measuring the electrical current at a first time and a second time later than the first time;
determining, in a computer, the threshold voltage in the ramped voltage at and above which the electrical current is faradaic, so that when the circuit generates and transmits an initialization voltage sequence to the working electrode, an initial voltage in the initialization voltage sequence is at least equal to, or within 5%, of the threshold voltage, so as to form the metal having a stable (steady state) charge distribution, wherein the determining comprises:

comparing the electrical current at the two different times; and selecting the threshold voltage as the lowest voltage in the voltage ramp for which the electrical current measured at the first time is higher than the electrical current measured at the second time.

17. The method of claim 16, wherein:

the circuit comprises a potentiostat connected to a voltage generation circuit, the voltage generation circuit generates and inputs the initialization voltage to the potentiostat, the potentiostat transmits the initialization voltage to the electrode, and the ramped voltage and the initialization voltage sequence each comprise a staircase voltage, the method further comprising:

adjusting a voltage step in the initialization voltage sequence so that the voltage is ramped in less than 1 hour from the initial voltage to a final voltage at which the potentiostat is biased when the electrical current provides a reliable measure the analyte's concentration during steady state operation.

* * * * *